ns011466251B2

United States Patent
Luettge et al.

(10) Patent No.: US 11,466,251 B2
(45) Date of Patent: Oct. 11, 2022

(54) 3D SPATIALLY ORGANIZED CULTURED NEURONAL TISSUE BY MEANS OF STACKING BEADS COMPRISING HYDROGEL ENCAPSULATED CELLS

(71) Applicant: Technische Universiteit Eindhoven, Eindhoven (NL)

(72) Inventors: Regina Luettge, Enschede (NL); Alex Jeroen Bastiaens, Eindhoven (NL); Jelle Jan Freerk Sleeboom, Utrecht (NL)

(73) Assignee: Technische Universiteit Eindhoven, Eindhoven (NL)

( * ) Notice: Subject to any disclaimer, the term of this patent is extended or adjusted under 35 U.S.C. 154(b) by 1072 days.

(21) Appl. No.: 15/781,794

(22) PCT Filed: Dec. 6, 2016

(86) PCT No.: PCT/EP2016/079961
§ 371 (c)(1),
(2) Date: Jun. 6, 2018

(87) PCT Pub. No.: WO2017/097788
PCT Pub. Date: Jun. 15, 2017

(65) Prior Publication Data
US 2018/0355314 A1    Dec. 13, 2018

Related U.S. Application Data

(60) Provisional application No. 62/263,807, filed on Dec. 7, 2015.

(51) Int. Cl.
*C12N 5/0793* (2010.01)
*C12M 3/00* (2006.01)
(Continued)

(52) U.S. Cl.
CPC .......... *C12N 5/0619* (2013.01); *C12M 21/08* (2013.01); *C12M 23/16* (2013.01); *C12M 25/16* (2013.01);
(Continued)

(58) Field of Classification Search
CPC .. C12N 5/0619; C12N 5/0012; C12N 5/0068; C12N 11/04; C12N 13/00;
(Continued)

(56) References Cited

U.S. PATENT DOCUMENTS 7,186,557 B2 * 3/2007 Marko .................... A61P 25/04
435/377
8,327,726 B2 * 12/2012 Kim .................... B01L 3/50273
73/864.81
(Continued)

FOREIGN PATENT DOCUMENTS

WO    WO2007094929    8/2007

OTHER PUBLICATIONS

Heo et al. Effects of the monomeric, oligomeric, and fibrillar Ab42 peptides on the proliferation and differentiation of adult neural stem cells from subventricular zone. Journal of Neurochemistry (2007), 102, 493-500. (Year: 2007).*
(Continued)

*Primary Examiner* — Sean C. Barron
(74) *Attorney, Agent, or Firm* — Lumen Patent Firm

(57) ABSTRACT

Culturing of organized 3D networks of neuronal cells is provided. Individual neuronal cells are encapsulated in gel beads. The gel beads are self-assembled into ordered structures in a bioreactor. Subsequent culturing of the cells in the bioreactor leads to the formation of an organized 3D network of the neuronal cells. Such structures have many applications, especially for as says of neuronal network function and/or structure.

13 Claims, 15 Drawing Sheets

(51) Int. Cl.
C12M 1/12 (2006.01)
C12N 5/00 (2006.01)
C12M 3/06 (2006.01)
C12N 11/04 (2006.01)
C12N 13/00 (2006.01)

(52) U.S. Cl.
CPC ......... *C12N 5/0012* (2013.01); *C12N 5/0068* (2013.01); *C12N 11/04* (2013.01); *C12N 13/00* (2013.01); *C12N 2513/00* (2013.01); *C12N 2535/00* (2013.01)

(58) Field of Classification Search
CPC ........... C12N 2513/00; C12N 2535/00; C12M 21/08; C12M 23/16; C12M 25/16
See application file for complete search history.

(56) References Cited

U.S. PATENT DOCUMENTS

2005/0069572 A1 3/2005 Williams et al.
2007/0134209 A1 6/2007 Oakey
2008/0031774 A1* 2/2008 Magnant .......... G01N 35/00722
422/63

OTHER PUBLICATIONS

Frimat et al., "Advances in 3D neuronal cell culture", 2015, JVST B 33(6), pp. 06F902:1-6.
Schurink et al., "Hydrogel/poly-dimethylsiloxane hybrid bioreactor facilitating 3D cell culturing", 2013, JVST B 31(6), pp. 06F903:1-5.
Li et al. Culture of Neural Stem Cells in Calcium Alginate Beads, Biotechol. 2006(22): 1683-1689.
Morimoto et al. Three-dimensional cell culture based on microfluidic techniques to mimic living tissues. Biomaterials Science 2013(1): 257-264.
Li et al. Encapsulated Neural Stem Cell Neuronal Differentiation in Fluorinated Methacrylamide Chitoson Hydrogels. Annals of Biomedical Engineering 2014(42:7): 1456-1469.
Frega et al. Network dynamics of 3D engineered neuronal cultures: a new experimental model for in-vitro electrophysiology. Science Reports 2014:4 1:14.
Tsuda et al. Monodisperse Cell-Encapsulated Peptide Microgel Beads for 3D Cell Culture. Langmuir 2010 26 (4) 2645-2649.

* cited by examiner

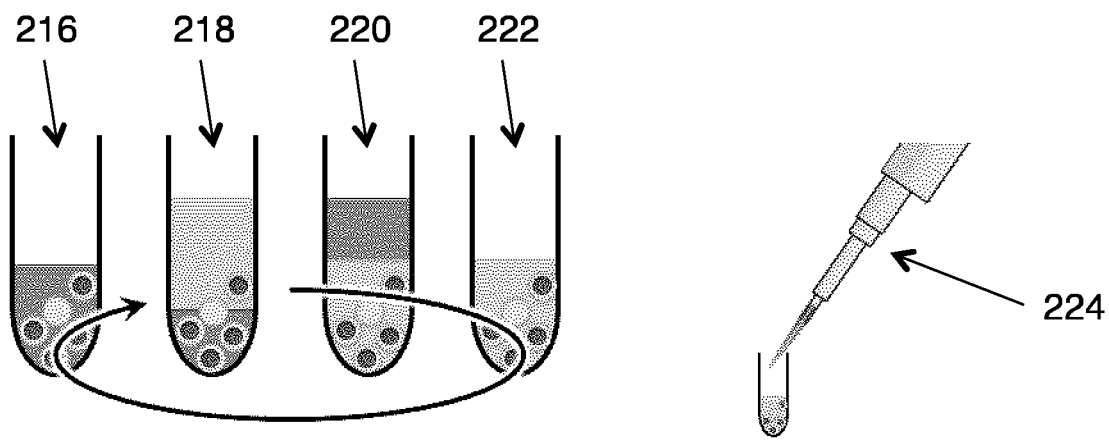
FIG. 2F
FIG. 2G
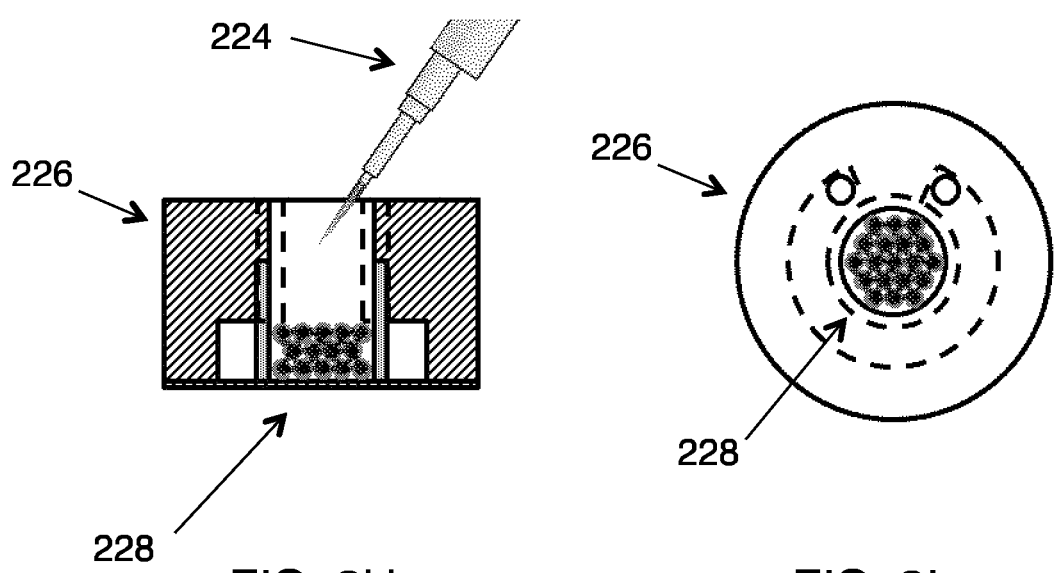
FIG. 2H
FIG. 2I

3D SPATIALLY ORGANIZED CULTURED NEURONAL TISSUE BY MEANS OF STACKING BEADS COMPRISING HYDROGEL ENCAPSULATED CELLS

CROSS-REFERENCE TO RELATED APPLICATIONS

This application is a 371 of PCT application PCT/EP2016/079961 filed on Dec. 6, 2016. PCT/EP2016/079961 claims the benefit of US Provisional application 62/263807 filed on Dec. 7, 2015.

FIELD OF THE INVENTION

This invention relates to culturing of neuronal cells, especially in the form of ordered networks of neuronal cells.

BACKGROUND

Brain diseases and disorders, such as epilepsy and Alzheimer's, are becoming more prevalent in the general population. However, no adequate treatments or therapies are currently available, mainly due to a lack of understanding of the underlying mechanisms. Since conventional research methods, such as animal models and 2D tissue cultures, do not capture the complexity of human physiology, new methods are needed to study the human brain.

Therefore, brain on a chip technology is currently being developed, to obtain more knowledge about the physiology of both the healthy and diseased human brain. Work to date has demonstrated ordered 2D and random 3D networks of neuronal cells. Thus it would be an advance in the art to provide an ordered 3D network of neuronal cells

SUMMARY

More specifically, the main goal is to create a chip in which human neuronal cells can be cultured in a 3D configuration and under physiological conditions, while they can be analyzed using both optical and electronic measurement methods. One of the main challenges is to engineer a system that promotes the formation of a physiologically relevant neuronal network, while retaining the controllability, observability, and reproducibility of organ-on-a-chip technology.

In this work, a new approach is provided to control the 3D spatial distribution of neuronal cells, based on the encapsulation of single cells in hydrogel beads and subsequent self-assembly to create an organized three-dimensional tissue.

To achieve single cell encapsulation, a microfluidic flow-focusing chip with implemented temperature control was engineered, in which cells can be encapsulated in Matrigel® droplets with a dispersity of approximately 2%. Cell encapsulation took place at a temperature below 4° C., after which gelation was initiated by transporting the droplets to a region at 37° C. on the same chip. The cells are shown to survive the encapsulation process, and remain viable over at least 11 days, as shown by live/dead staining.

Here Matrigel® is the trade name for a gelatinous protein mixture secreted by Engelbreth-Holm-Swarm (EHS) mouse sarcoma cells produced and marketed by Corning Life Sciences and BD Biosciences. Trevigen, Inc. markets their own version under the trade name Cultrex BME. Matrigel® resembles the complex extracellular environment found in many tissues and is used by cell biologists as a substrate (basement membrane matrix) for culturing cells. Any other hydrogel suitable for cell encapsulation can also be used in practicing embodiments of the invention.

Moreover, the cells retain their potential for differentiation inside the Matrigel® beads, as indicated by the formation of neurites and inter-cellular connections in the established 3D cultures. Self-organization of the manufactured beads was demonstrated inside oil, and recommendations are provided for microfluidic approaches to achieve self-assembly in cell culture medium.

The method can be applied in a three-dimensional bioreactor for neuronal cell culture to enhance the experimental reproducibility, facilitate the formation of a 3D spatially standardized neuronal network, and enable advanced co-culture brain models. Additionally, the method can be applied to enhance spatial organization in other organ-on-a-chip applications.

BRIEF DESCRIPTION OF THE DRAWINGS

FIGS. 2A-2I show an exemplary processing sequence for practicing an embodiment of the invention.

DETAILED DESCRIPTION

Section A describes general principles relating to embodiments of the invention, and section B describes relevant experimental work.

A) General Principles

FIGS. 1A-D schematically show the main ideas of an exemplary embodiment of the invention. In this example, living neuronal cells 110 are encapsulated with a gel 112 to provide hydrogel beads. A neuronal cell, as defined herein, means a cell found in the tissue of the nervous system, e.g., neurons. This definition also includes supporting cells, such as glia cells, specifically astrocytes and oligodendrocytic cells. Such cells can be derived from various sources.

Figure 1A:
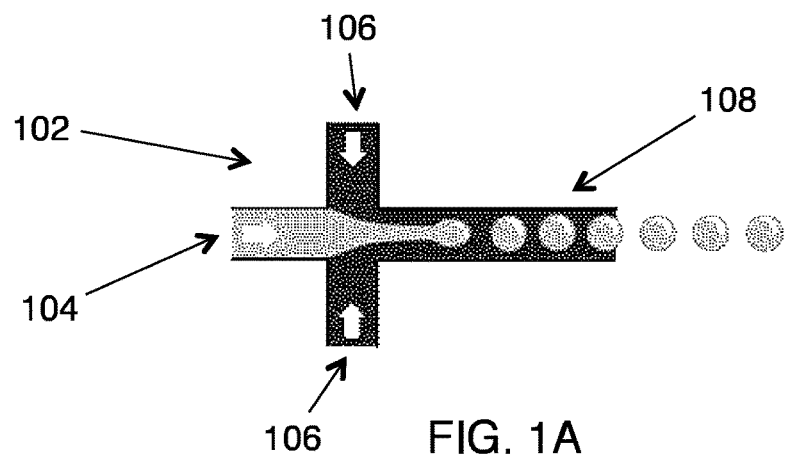
FIGS. 1A-D schematically show the main ideas of an exemplary embodiment of the invention.
Figure 1B:
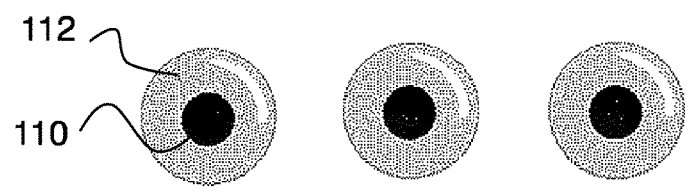
Figure 1C:
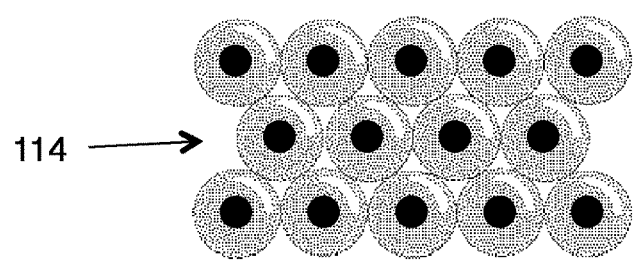

In a non-limiting example, this encapsulation can be performed as shown on FIG. 1A. Here a first mixture 104 and a second mixture 106 are provided to microfluidic apparatus 102. First mixture 104 is gel precursor+cells and second mixture 106 is oil+surfactant. Microfluidic droplet generation of liquefied gel mixed with cells in channel 108 leads to a configuration where the second mixture separates zones of the first mixture. As described in greater detail below, the microfluidic apparatus preferably includes a cold zone where the first and second mixtures are input and a warm zone where the gel precursor changes from a liquid to a gel, thereby forming the hydrogel beads with encapsulated cells. The cold zone preferably has a temperature in a range from 1-4° C. The warm zone preferably has a temperature in a range from 10-38° C.

Figure 1D:
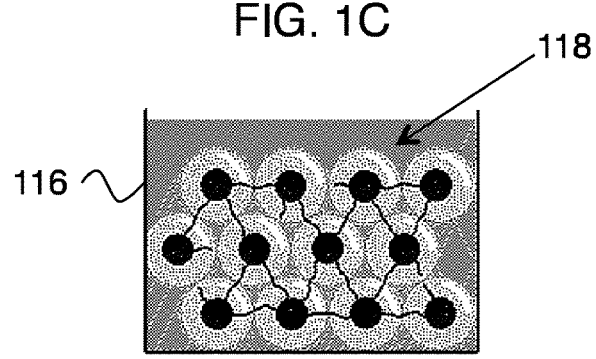

The hydrogel beads can self-assemble to create a well-defined three-dimensional organization of beads (e.g., 114 on FIG. 1C) within a bioreactor (e.g., 116 on FIG. 1D). Culturing the ordered arrangement of the hydrogel beads within the bioreactor leads to a configuration such that living neuronal cells in different hydrogel beads link with each other to form a network of neuronal cells (e.g., 118 on FIG. 1D). The encapsulated living neuronal cells can differentiate during the culturing of the ordered arrangement of the hydrogel beads within the bioreactor.

Figure 1E:
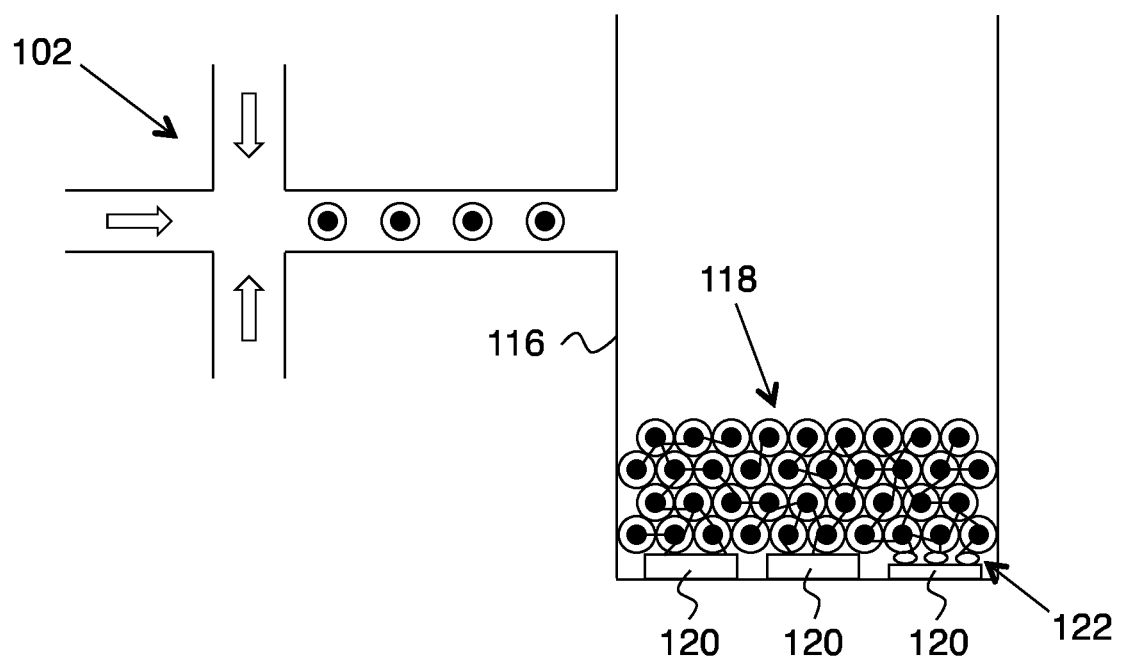
FIG. 1E shows an alternative bioreactor configuration.

FIG. 1E shows an exemplary embodiment having several optional features. In this example, microfluidic apparatus 102 for forming encapsulated cells can be integrated with bioreactor 116. Bioreactor 116 can include electrodes 120 configured to make electrical contact with the network of neuronal cells 118. The bioreactor can further include one or more living cells 122 disposed on one or more of the electrodes and configured to act as transducer cells for the network of neuronal cells.

An important application of the present technology is performing assays. In general, an assay is an evaluation of the response of a test system to exposure to the target analyte. The analyte can be biological, chemical or physical (mechanical, electrical, magnetic, optical, thermal). The test system in this case is the network of neuronal cells, which can be evaluated in terms of its function (e.g., electrical responses to provide an electrophysiological assay) and/or its structure (e.g., number of neuronal connections formed in the network, or degree of disordering upon exposure). This provides a qualitatively new kind of assay capability compared to assays where the test system is not an organized network of neuronal cells.

We believe that order/disorder in a neuronal network is a measure of neuronal network plasticity (this appears to be also happening in the living brain); and disorder may act as a biomarker for deficiency of the brain. The in vitro system can then emulate this state of brain, and neurological functions in the systems can be modulated using a variety of stimuli. Drugs, for example, modulate the neurological functions at the molecular level but also locally applied electrical potentials can be used as stimuli for modulation of neuronal tissue (as demonstrated by various approaches to deep brain stimulation using an electrode implanted into the brain). These physical methods allow for novel treatment modalities in brain disorders and are currently being clinically investigated. An advanced in vitro system of the brain, as considered herein is an example of such an in vitro system and can be used to evaluate treatment modalities pre-clinically without using test animals.

B) Experimental Work

Figure 2A:
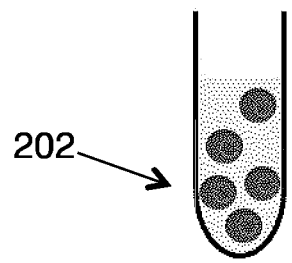
Figure 2B:
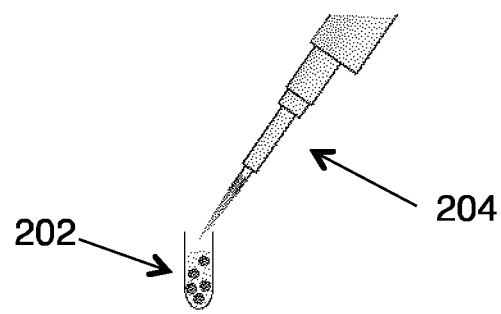
Figure 2C:
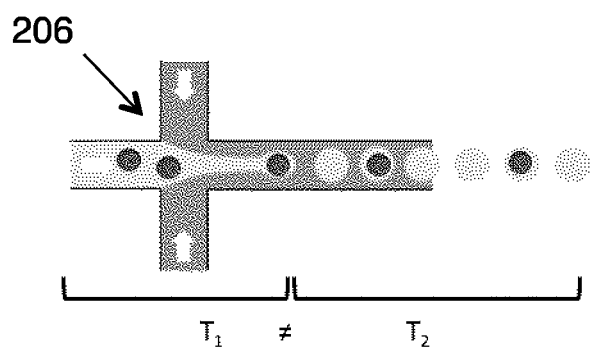
Figure 2D:
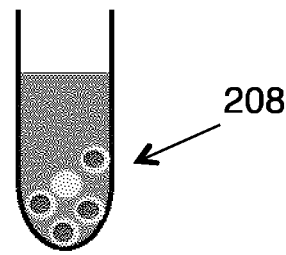

FIGS. 2A-2I show an exemplary processing sequence for making an organized network of neuronal cells using cell encapsulation and self-assembly. Here 202 on FIG. 2A is a mixture of cells and a gel precursor that is liquid at low temperatures and a gel at warm temperatures. FIG. 2B shows transfer of this mixture to a pipette 204. This pipette is used to transfer this mixture to a microfluidic apparatus 206 on FIG. 2C. This creates gel precursor droplets containing cells which warm up to form gel beads containing cells. Beads in oil 208 on FIG. 2D are collected from the microfluidic apparatus 206.

Figure 2E:
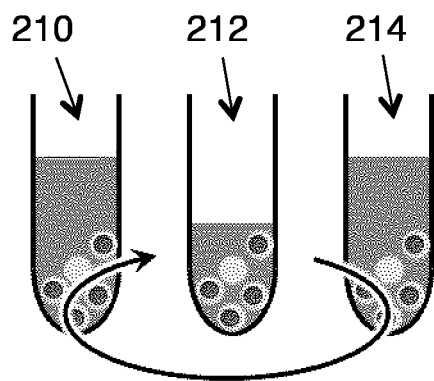

Repetitive washing steps with oil 210, 212, 214 on FIG. 2E are performed to remove the surfactant from the oil. Repetitive washing steps with cell culture medium 216, 218, 220, 222 on FIG. 2F are performed to remove the oil from the medium. The resulting configuration is hydrogel encapsulated cells disposed in cell culture medium. Beads and medium are then transferred using a pipette 224 on FIG. 2G to a bioreactor 226 on FIGS. 2H and 2I for culturing. In the bioreactor the beads will self-assemble to create an organized, three-dimensional, cell culture 228. These neuronal cells 228 will form a network over time which will then also be organized.

Figure 3:
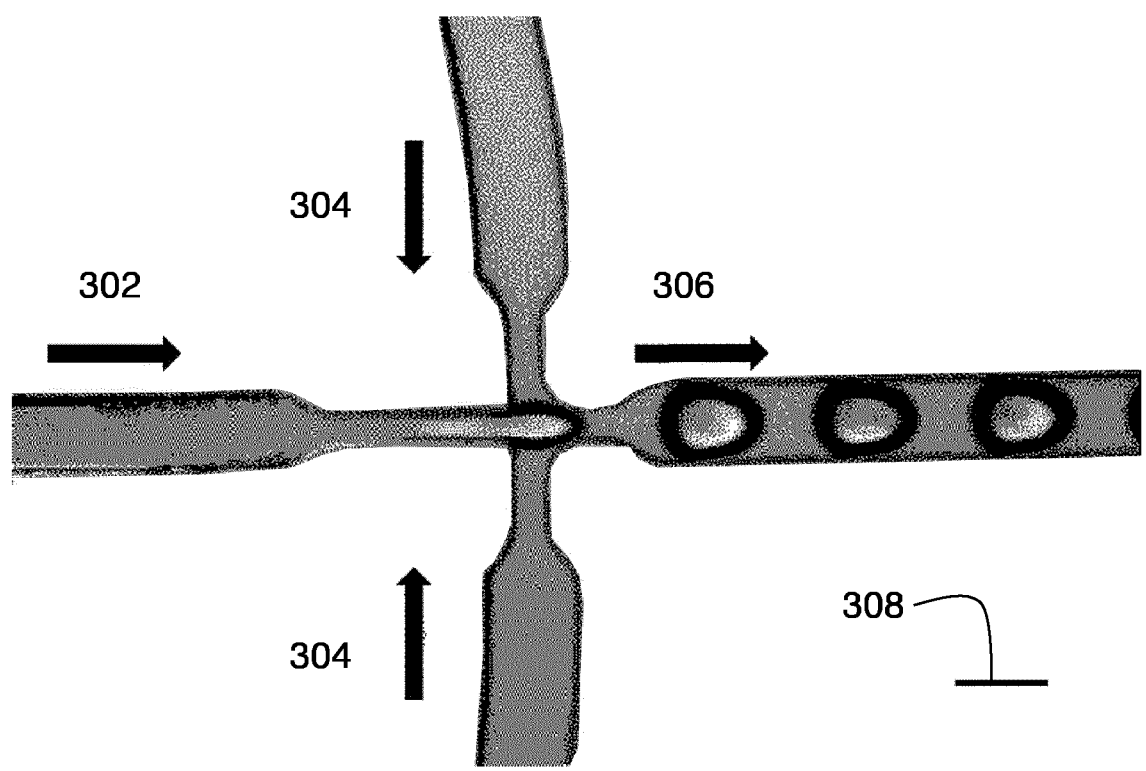
FIG. 3 shows an image of a microfluidic channel geometry for cell encapsulation in operation.

FIG. 3 shows an image of a microfluidic channel geometry for cell encapsulation in operation. In this example, liquefied, cooled, gel mixed with cells enters the flow-focusing section 302 from the left. Oil containing surfactant enters the flow-focusing section from the top and bottom (both referenced as 304). Monodisperse cell-laden beads of gel containing cells are generated at the right channel 306 through breaking up of the liquefied gel. Arrows indicate direction of flow, scale bar 308 is 100 µm.

Figure 4:
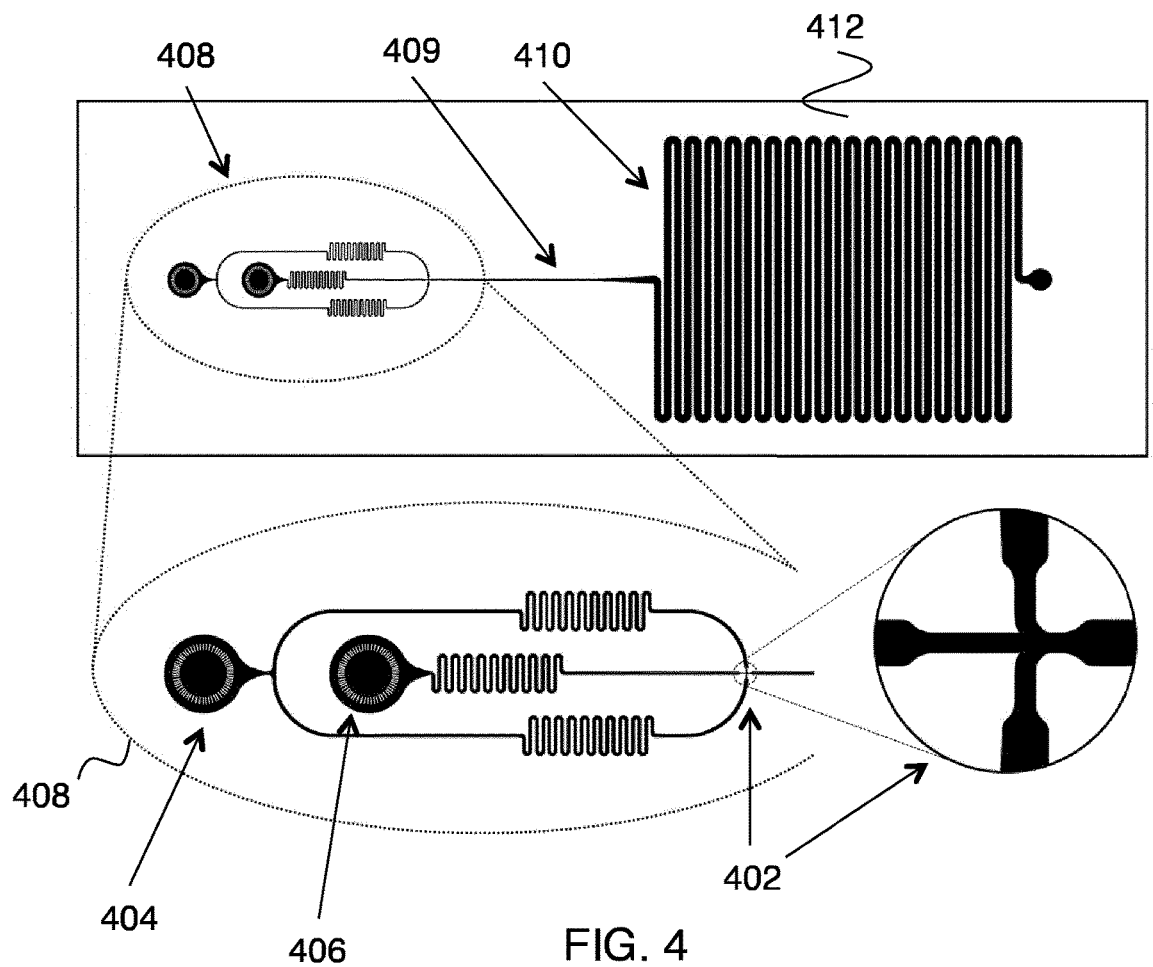
FIG. 4 is a top view of an exemplary microfluidic channel device for cell encapsulation.

FIG. 4 is a top view of an exemplary microfluidic channel device 412 for cell encapsulation. The mixing section 408 shows the inlets of the oil and cell-laden gel phase (404 and 406 respectively), meandering channels for temperature equilibration prior to the flow-focusing section, and the flow-focusing section 402 of the chip. An enlargement of flow-focusing section 402 is also shown. Both inlets contain a filtering pillar array with a spacing of 20 µm. The flow-focusing section contains an orifice width of 40 µm. After flow-focusing section 402 a straight channel section 409 provides for a controlled temperature increase for gel bead formation. After that a temperature-stable meandering channel section 410 provides temperature equilibration for the gel beads.

Figure 5:
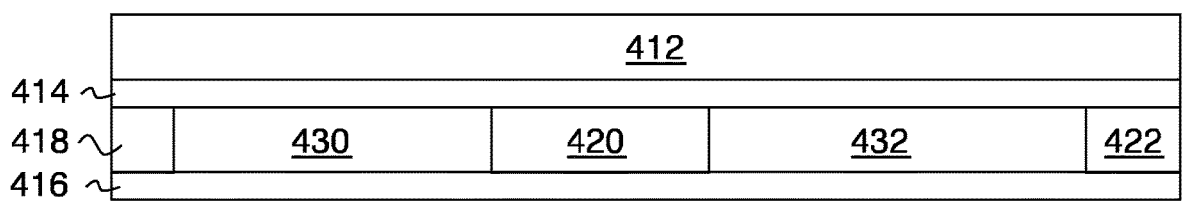
FIG. 5 is a cross section view corresponding to the top view of FIG. 4.

FIG. 5 is a cross section view corresponding to the top view of FIG. 4. The purpose of the structures under microfluidic channel device 412 on FIG. 5 is to provide temperature control for gel bead formation. In this example, a cool chamber 430 and warm chamber 432 are formed by sandwiching members 418, 420, 422 between top plate 414 and bottom plate 416. In one experiment, members 418, 420 and 422 were all made from Poly(methyl methacrylate) (PMMA), bottom plate 416 was PMMA and top plate 414 was a glass microscope slide.

Further details of the fabrication and characterization of this microfluidic apparatus are provided by way of example. The device was made of multiple layers (FIG. 5), using standard photo- and soft-lithography processes, combined with laser-cutting and gluing for the temperature control chambers.

First, a master-mold was made using photolithography, after which it was replicated in PDMS (Polydimethylsiloxane). This replica was then bonded to a microscope slide to finalize the microfluidic side of the device.

A wafer was cleaned by subsequently rinsing it with acetone, isopropanol, and ethanol, after which the wafer was dried with nitrogen gas. To further reduce the amount of liquid left on the wafer, it was put on a 95° C. hot plate for about 2 minutes. A 100 µm layer of photoresist (Microchem, SU-8 3050) was coated onto the cleaned wafer using a spin-coater (Laurell, WS-400B-6NPP-LITE).

The coated wafer was then baked on a 95° C. hot plate for 50 minutes, after which the photo-mask containing the channel design was placed on top of the wafer. The mask was covered by a clean glass plate and exposed to UV-light for 18 seconds, at 14 mW/cm$^2$. After exposure, the wafer was placed on a hot plate at 65° C. for 1 minute, followed by a 5 minute bake on a 95° C. hot plate to initiate cross-linking.

The wafer was then developed in a bath filled with developer (Micro Resist Technology, mr-dev 600) under constant agitation by an orbital shaker (Cole-Parmer, EW-51300-05). After 10 minutes, the developer was refreshed, and the wafer was developed for another 5 minutes.

PDMS base and curing agent (Sylgard, 184) were mixed at a 10:1 ratio using a planetary centrifugal mixer (Thinky, ARE-250) at 2000 rpm for 1.5 minutes. A degassing step at 2000 rpm for 1 minute was included in the mixing protocol. The mixed PDMS was poured onto the master, and put under vacuum for approximately 1 hour, to remove any air bubbles from the cast. The filled mold was then put in an oven at 65° C. for at least 3 hours to cure the PDMS.

After curing, the PDMS was removed from the master and cut to separate the different devices. Inlet and outlet holes were punched using a 1.2 mm biopsy punch. The PDMS slabs were then bonded to a glass slide using a plasma surface activation method. Dust was removed from the PDMS slabs and microscope slides using some standard tape, after which both were exposed to an air plasma for 45 seconds (50 W, 0.6 mbar) in a plasma asher (Emitech, K1050X). The plasma treated slides and PDMS slabs were then carefully connected and put in an oven at 65° C. 1 hour to finalize the bonding process.

The walls of the temperature control chambers were made of Poly(methyl methacrylate) (PMMA), which has a thermal conductivity that is similar to that of PDMS. The bottom of the device was laser-cut into the shape of a microscope slide (25×75 mm) from 1 mm thick extruded PMMA plate. The layer forming the sidewalls of the temperature chambers was laser-cut from 3 mm thick extruded PMMA plate. In and outlets with a diameter of 2 mm were carefully drilled into the sides of the cut chamber sections. The two parts were then glued together using a slow curing silicone sealant (Dow Corning, Multi-purpose Sealant 732), which was applied using a 5 mL plastic syringe. After leaving the sealant to cure for at least 24 hours, the microfluidic side of the device was bonded to the assembled bottom section using the same sealant.

In this work, a device with integrated temperature control for the encapsulation of cells in Matrigel® was developed. First, a microfluidic chip was designed, having a flow-focusing section for Matrigel® droplet generation, and a meandering channel section where droplets are gelated to form beads. Temperature control chambers were added to this chip, to achieve a temperature below 4° C. at the flow-focusing section, such that liquid Matrigel® droplets can be generated, and a temperature above 10° C. at the meandering channel section to induce gelation.

Figure 6:
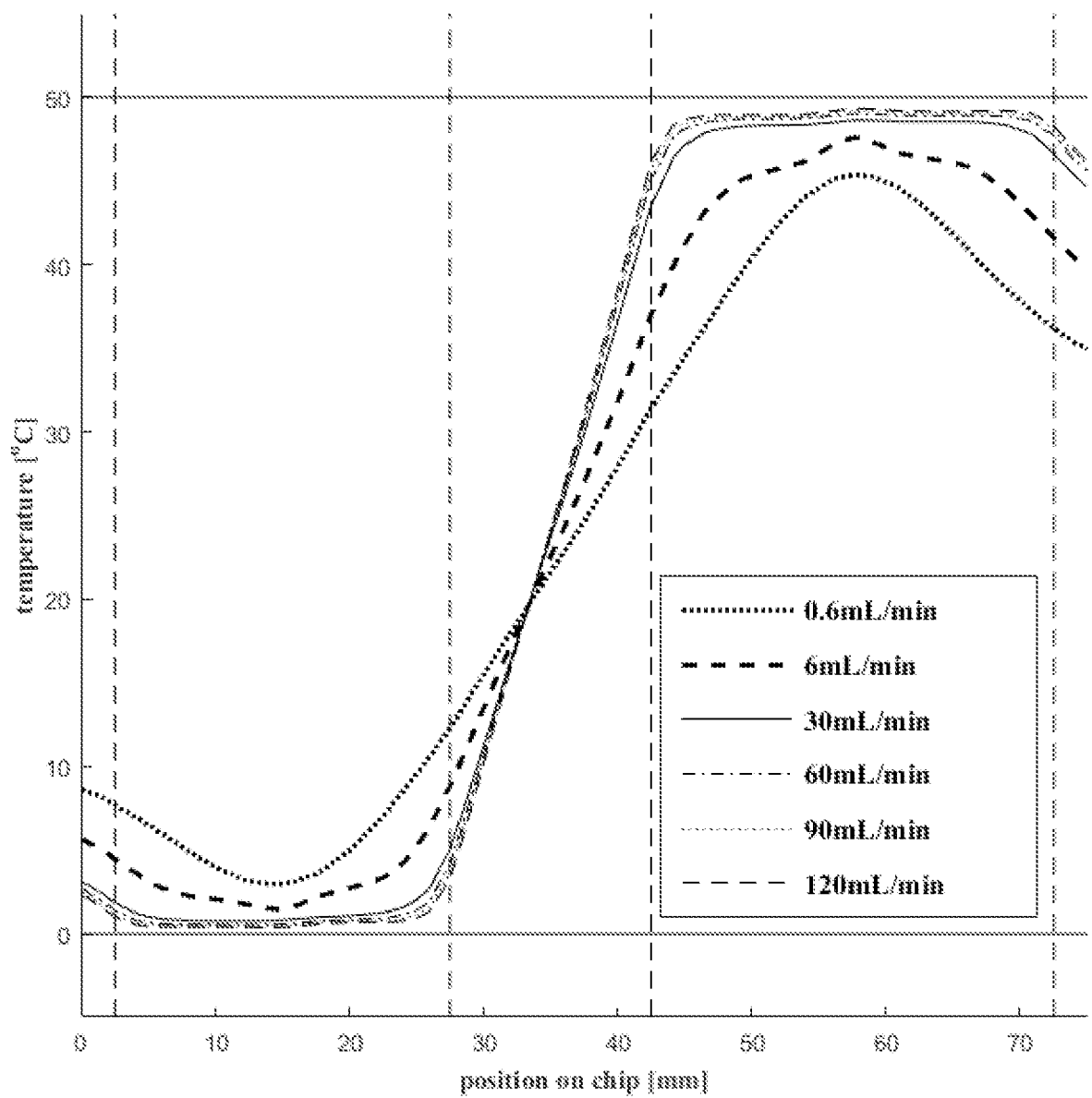
FIG. 6 is a plot showing simulated temperature vs. position on a microfluidic channel device at various flow rates.

The transition from liquid to gel can be assessed by evaluating the temperature profiles for all simulated flow-rates, along the center of the chip. FIG. 6 shows simulated temperature profile for flow rates between 0.6 and 120 mL/min. The dashed lines indicate the edges of the temperature chambers, and the solid black lines the set temperature at the inlets of these chambers: 0 and 50° C. The 0 and 50° C. temperatures used here are for convenience in testing the thermal performance of the device, and are not representative of temperature that would be used in connection with living cells.

For the simulated flow-rates of 0.6 and 6 mL/min, it is clear that the temperature curve has absolutely no constant regions. However, for flow-rates of 30 mL/min and up, the graph shows two regions with nearly uniform temperature. Moreover, towards the higher flow-rates, the temperature profile seems to converge to a fixed solution, although it never fully reaches the set temperatures at the chip inlets (0 and 50° C.). It is important to note that the temperature on top of the glass slide will never be equal to these temperatures, since the heat resistance of the slide prevents this from happening.

Another conclusion we can draw from these simulations is that the regions of constant temperature are slightly smaller than the temperature chambers. For the cold region this is acceptable, since the inlet and flow-focusing section are centered on the cold region, at sufficient distance from the edges. For the hot region, however, this means that the temperature is not constant over the entire meandering channel section. Especially near the bends in this section, temperature can be several degrees lower than in the center. Fortunately, this is negligible, since the exact temperature is not relevant for Matrigel® gelation, as long as it is higher than 10° C. Between the two temperature sections, there is an approximately linear transition between the low and high temperature, with a gradient that converges to approximately 2.9° C./mm.

Using these simulations, the feasibility of the temperature control strategy has been shown. At sufficiently high water flow-rates, vortices form inside the temperature chambers that distribute the heat or cold over the designated area. However, the simulations have only taken the chip itself into account, assuming perfect heat transfer between the materials that comprise the chip. In order to fully validate the approach, including possible heat losses in the auxiliary equipment and tube connections, temperature measurements are required. Additionally, calibration of the reservoir temperatures is important for setting the correct temperature.

Figure 7:
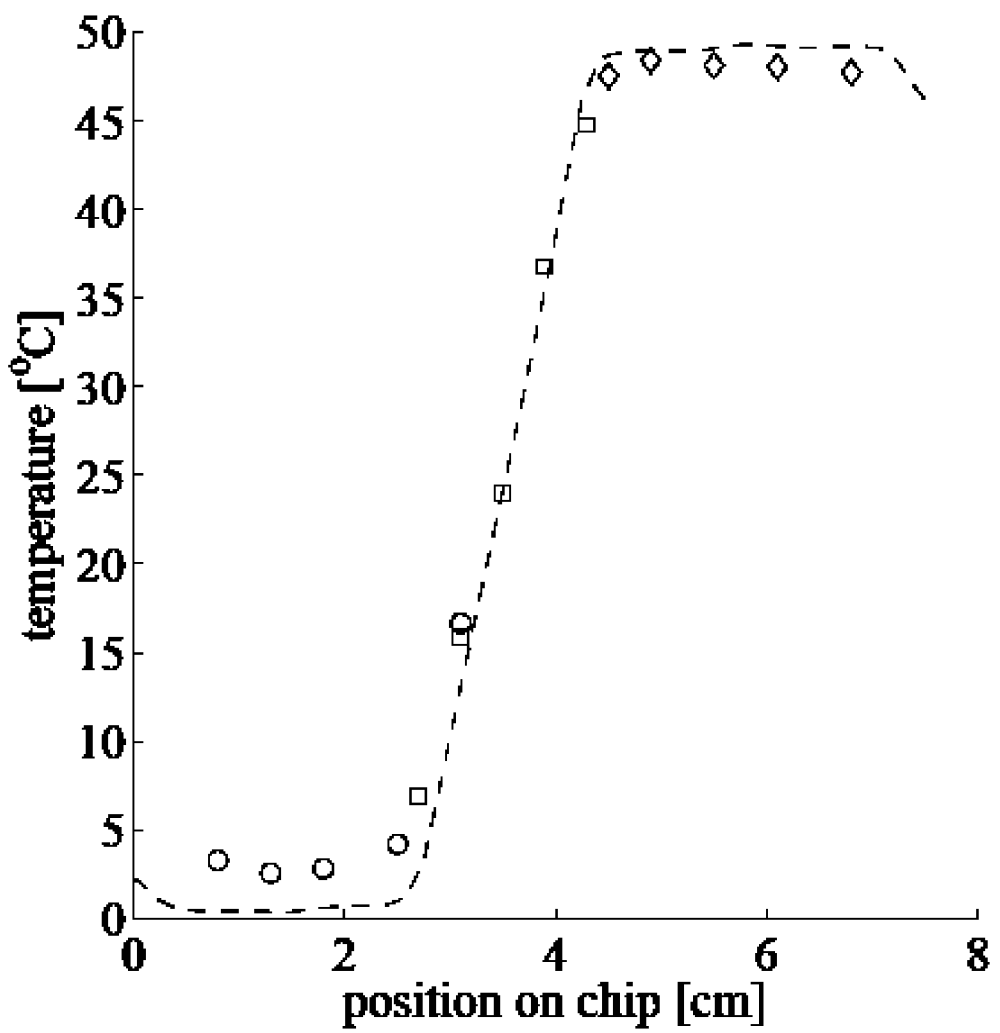
FIG. 7 is a plot showing a comparison of measured and simulated temperature vs. position on a microfluidic channel device.

Temperature measurements were performed on the temperature control chambers, for comparison with the simulated temperature profile of FIG. 6. The measured temperature profile on the chip for reservoir temperatures of 0 and 50° C. is shown on FIG. 7. The profile was determined from 3 separate measurements: on the cold chamber, between the chambers, and on the hot chamber. The corresponding temperature curve obtained from the simulation is shown as a dashed line.

The temperature profile for reservoir temperatures of 0 and 50° C. was in good agreement with the simulated profile in terms of the profile shape. Both regions of constant temperature and the linear temperature gradient are present in the data.

However, there are several deviations from the simulated profile, such as the higher temperature at the cold chamber (approximately 2.5° C. higher), and the slightly lower temperature at the hot chamber (approximately 1° C. lower). These differences between theory and practice can be attributed to both limits of the simulation and physical error sources. Despite the deviations between the simulation and the measured profile, the temperature of the cold region is below 4° C., which is sufficient for having liquid Matrigel® inside the device.

Figure 8A:
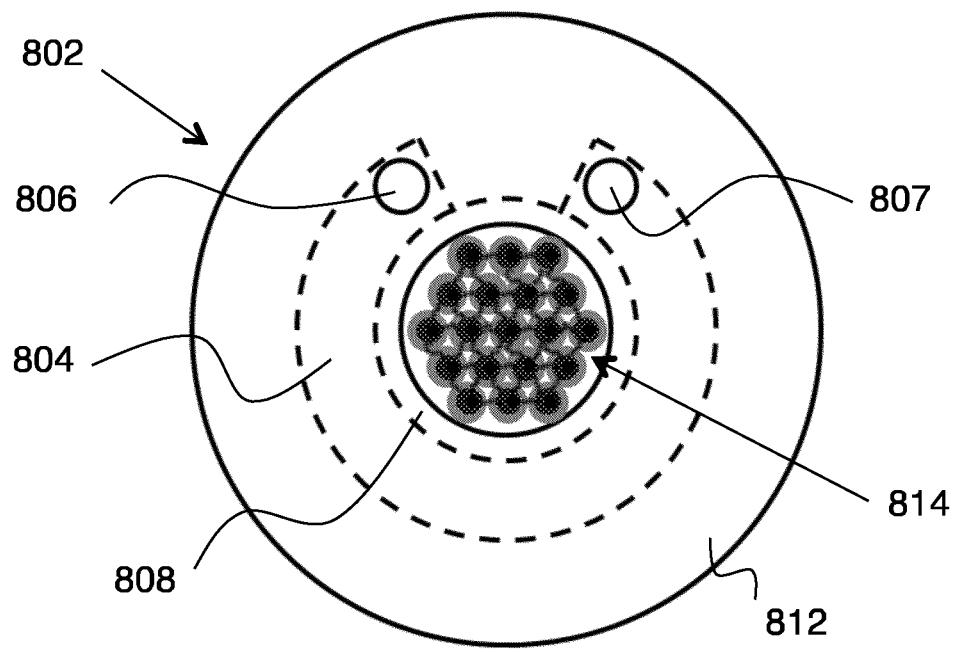
FIGS. 8A-B show a preferred bioreactor configuration.
Figure 8B:
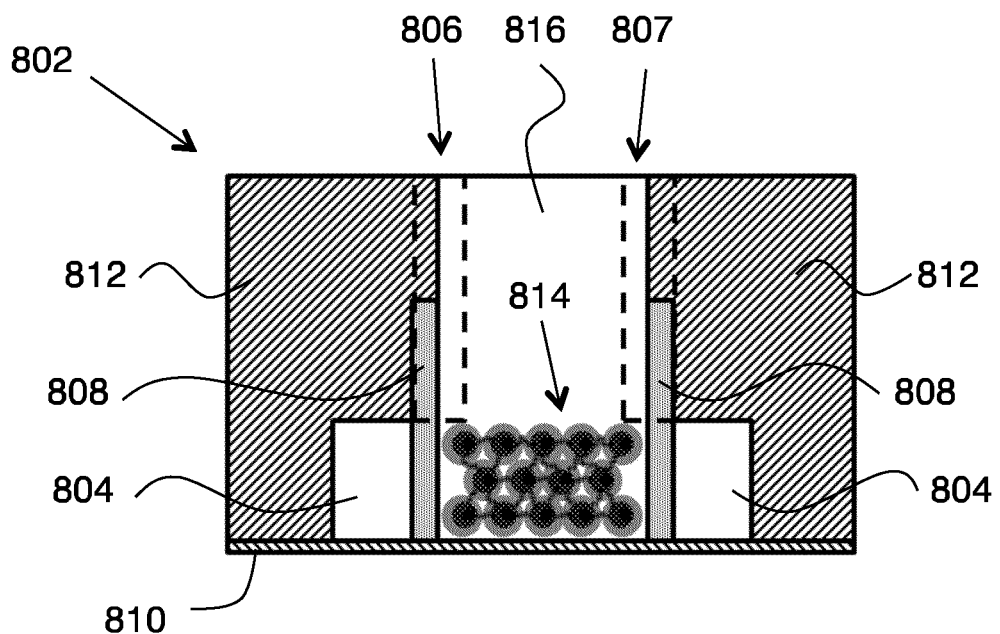

FIGS. 8A-B show a preferred bioreactor configuration. Here FIG. 8A is a top view and FIG. 8B is a corresponding cross-sectional view of an organized, three-dimensional, bead-based neuronal cell culture in a microbioreactor 802. The bioreactor may be either set up with an open culture chamber 816 for easy pipetting or with a closed culture chamber only containing inlet and outlet channels in the top layer. Here an open chamber 816 is depicted by way of example. A cylinder 808 (typical inside diameter of 1 mm to 5 mm) of porous material (e.g., Agarose) acts as an interface between the cell culture chamber and a microfluidic channel 804, where the porous material 808 allows for medium and waste exchange into and from the culture chamber via inlet 806 and outlet 807. The culture chamber 816 is open at the bottom to allow different substrates 810 to connect to the culture, e.g. a microelectrode array for electrophysiological assays or a thin glass slide for optical assays. Bioreactor wall 812 is preferably at least 0.5 mm thick to permit such attachment to substrate 810. Placing bead-encapsulated neuronal cells 814 into the culture chamber will lead to a self-assembled stacking of the encapsulating beads that can be cultured to a state where an organized network of neuronal cells will be formed.

The significance of using such construction is that we allow for sufficient diffusion throughout the entire culture volume. Hence we could stack multiple cell layers up to a proven height of 400 microns; here we only demonstrated this with one cell type. The tissue which forms should then be more brain-like since the space between neuronal cells can be filled with extracellular matrix. A second aspect is that the PDMS microbioreactor can be designed as an add-on for Micro (or multi)-electrode arrays.

An important aspect of this microbioreactor design is to be able to interconnect the 3D cell-laden bead structure with a defined footprint atop of the footprint of an electrode array instead of the general carpet like structure known from 2D cultures, and still allow for a suitable number of cells required for a firing network with a high number of ordering (due to the stacking in the cylindrical cell culture chamber). By extending the culture in its height we can make use of a microfluidic feedstock and waste removal via the porous wall of the cell culture chamber in our design. The restricted diameter allows for fewer mistakes in the order of the network.

Large area cultures do not allow multilayer culture due to the diffusion limitations for providing nutrients and removing waste. The porous wall of the cylinder may also be realized by a biological membrane structure representing more closely the neurovascular system. Utilizing soft material for the channel structure may also allow one to emulate pulsating flows similarly to conditions under blood flow. Classical well plates do not offer any such capability.

Figure 9A:
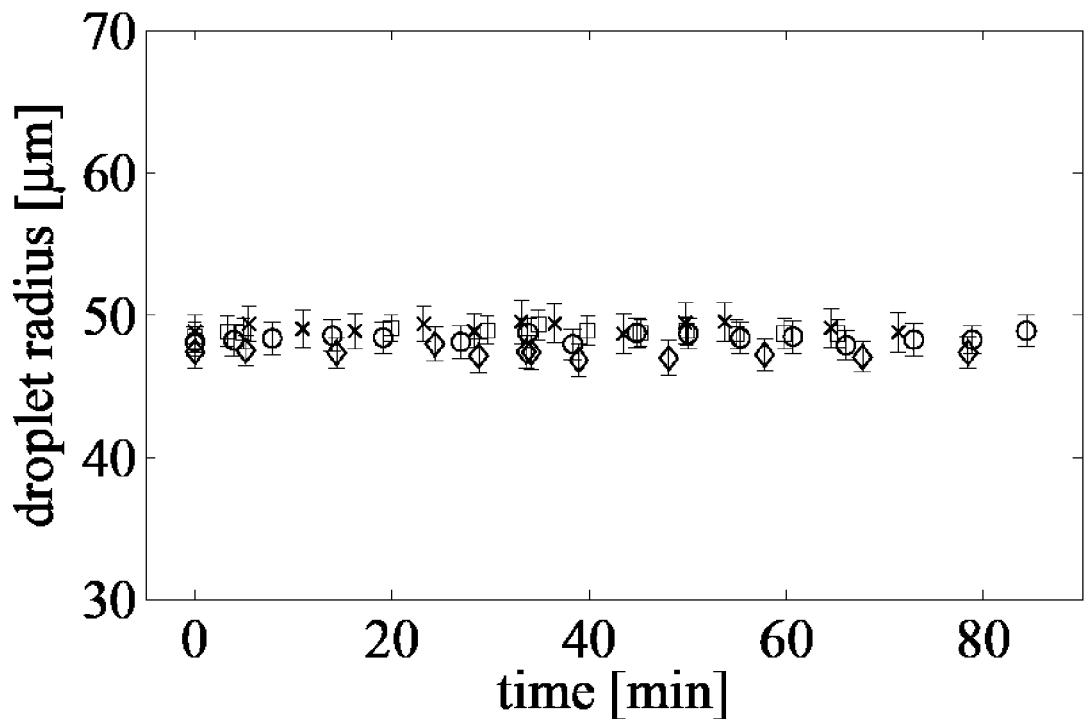
FIG. 9A is a plot of gel bead radius vs. time for a gel bead generation process.
Figure 9B:
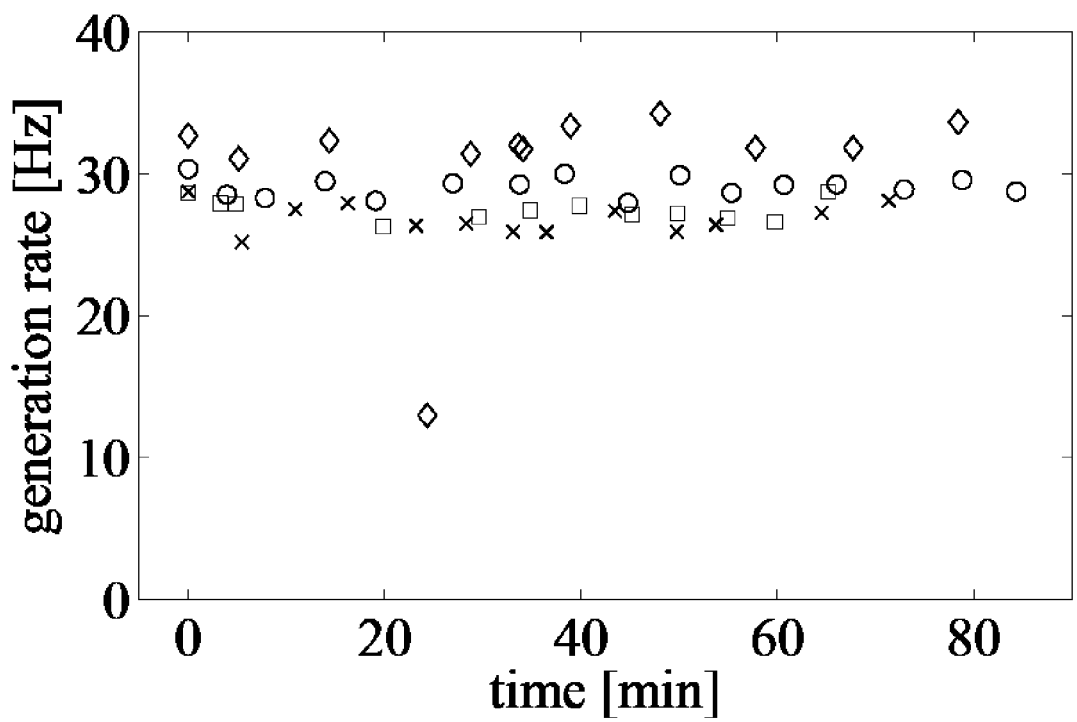
FIG. 9B is a plot of gel bead generation rate corresponding to FIG. 9A.

The above described microfluidic device is capable of providing highly uniform gel beads. FIG. 9A is a plot of gel bead radius (referred to as droplet radius on the figure) vs. time for a gel bead generation process in four experimental runs. Error bars indicate the standard deviation, which is approximately 1 μm for all radius measurements. The average gel bead radii for the four runs shown are 48.4 μm, 48.8 μm, 47.3 μm, and 49.1 μm respectively. FIG. 9B is a plot of gel bead generation rate corresponding to FIG. 9A. The low generation rate data point at 13 Hz is the result of a coalescence event, which is omitted from the average. The average generation rates and standard deviations for the four runs are 29.1±0.7 Hz, 27.5±0.8 Hz, 32.5±1 Hz, and 26.9±1.1 Hz respectively.

Gel bead radii were determined over the course of the experiment from recorded videos of moving gel beads inside the meandering channel. Additionally, the gel bead generation frequency was derived by dividing the number of counted gel beads by the duration of each movie.

When comparing the average radii of the four different experiments, excellent reproducibility is observed: All devices generate gel beads of almost exactly the same diameter. Moreover, all experiments are in a stable generation regime, since the gel bead radii hardly vary over the duration of the experiment. The dispersity of the gel beads, computed by dividing the standard deviation by the average radius, varies between 2 and 3% for all experiments. This shows that the gel beads are highly monodisperse.

The generation rate, much like the average radius, varies slightly between experiments. A lower gel bead radius corresponds to a higher generation rate. This is in agreement with the fact that all experiments were conducted with the same flow-rates. It is important to note that one of the frequency measurements deviates significantly from the others. This is the result of a coalescence event upstream of the measurement position, which causes temporary blockage of the meandering channel, and therefore temporary depletion of gel beads in the measurement section. Since in this section, the gel bead generation rate and dispersity are investigated, this measurement is excluded from all the computed averages. However, the coalescence event does influence the dispersity of the beads that are retrieved from the device.

In conclusion, the encapsulation device enables the stable, reproducible generation of monodisperse gel beads with a dispersity<3%. The overall average gel bead generation rate is 29 Hz, which means that for the duration of an entire experiment (±90 minutes), approximately $1.57 \times 10^5$ gel beads are generated, with an average radius of 48.4 μm. Since the aim was to produce beads with a diameter of 100 μm, and an average diameter of 96.8 μm is achieved, this design is usable for further experiments.

Figure 10:
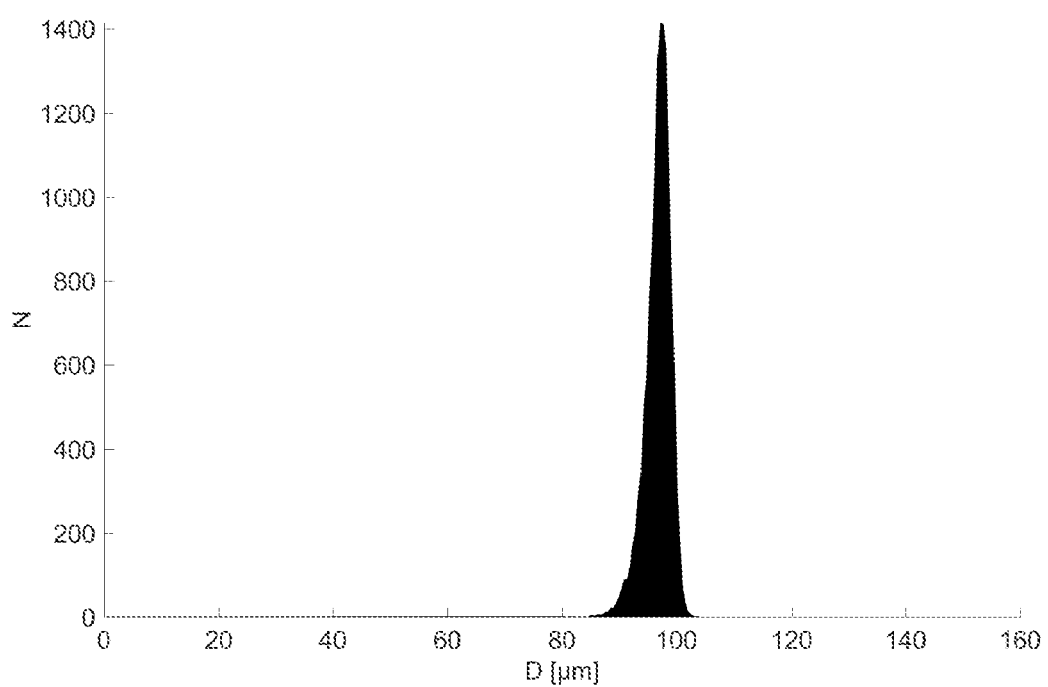
FIG. 10 is a histogram of gel bead diameter.

FIG. 10 is a histogram of the gel bead diameters during a cell encapsulation run in one device, as measured by image analysis of a microscopic video recording. From this it can be determined that gel beads are generated with a dispersity<3%.

Figure 11:
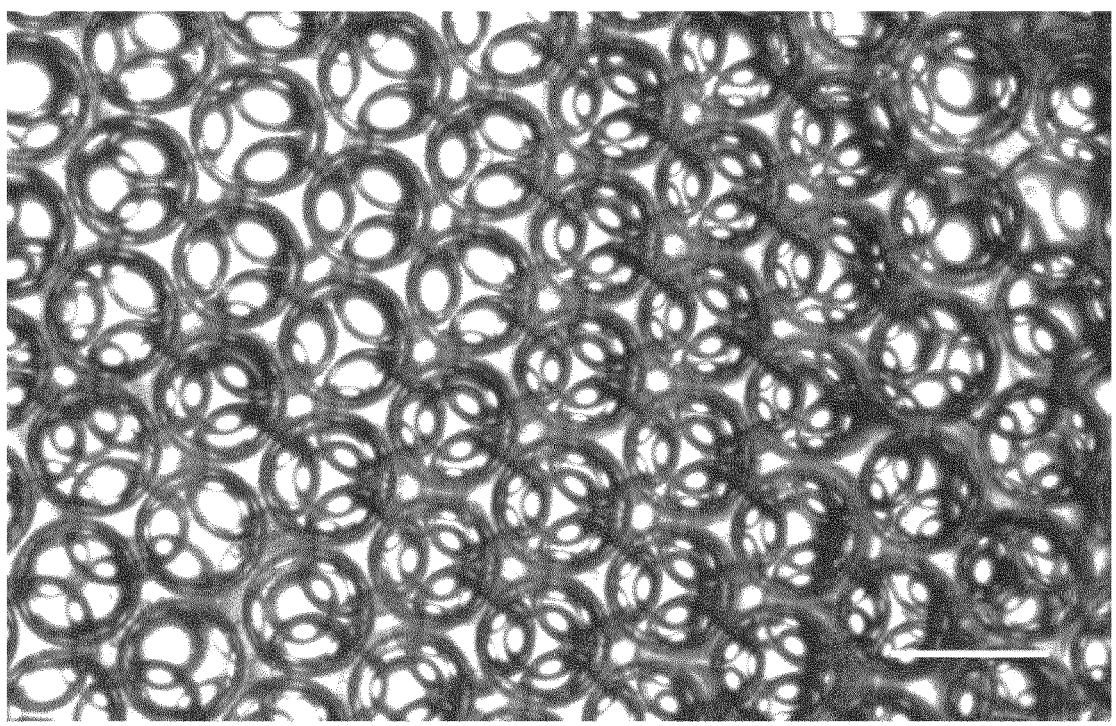
FIG. 11 is an image of hydrogel beads stacked in oil.

FIG. 11 is an image of hydrogel beads stacked in oil. This is an image of the Matrigel® beads stacked in mineral oil, exhibiting a hexagonally close packed structure in 3D.

Figure 12:
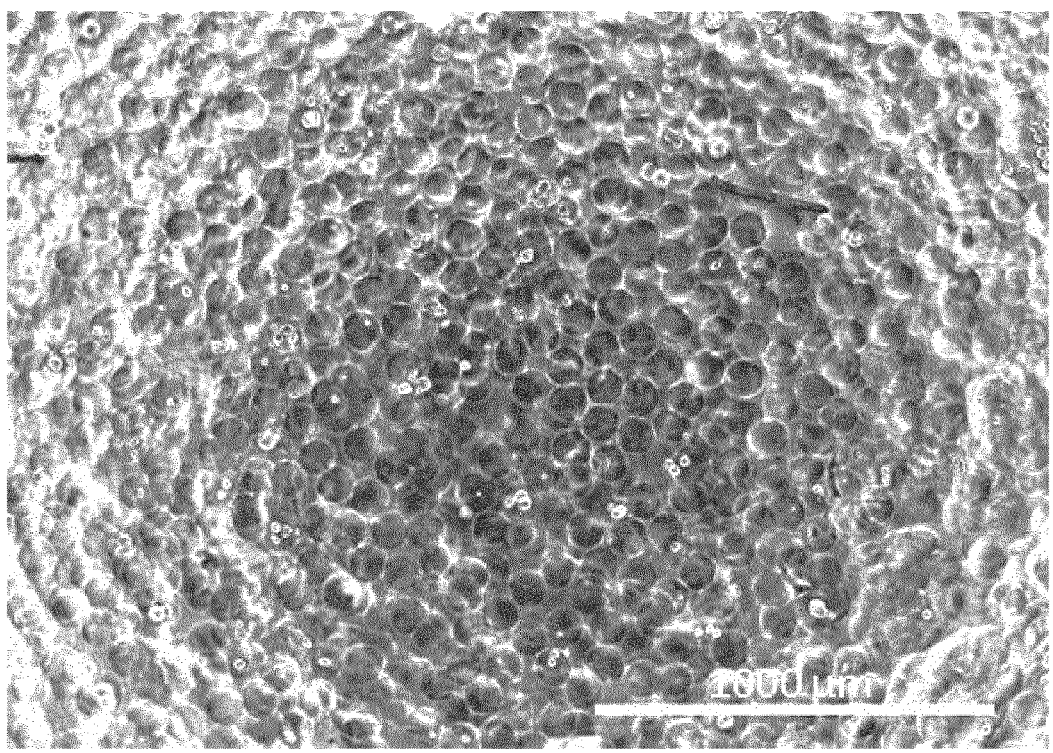
FIG. 12 is an image of hydrogel beads stacked in medium.

FIG. 12 is an image of hydrogel beads stacked in medium. This shows encapsulated cells stacked in culture medium, showing organized beads in 3D.

By way of example, further details relating to cell encapsulation in these experiments are provided. Before cell encapsulation, the temperature control section of the setup was filled with water and set to appropriate temperatures. First, the chip outlet was connected to a sterile Eppendorf tube, and covered with a layer of Parafilm (Parafilm, PM-996) to reduce the chance of infection. For the continuous phase, mineral oil (Sigma, M8410) containing 4 wt. % of a polysiloxane surfactant (Evonik Industries, ABIL EM 90) was aspirated into a 1 mL plastic syringe (Terumo). The syringe was installed on a syringe pump (Chemyx, Nexus 3000), and connected to the continuous phase inlet using a 20 GA needle tip (Techcon Systems, TE720050PK). Most of the inlet tube was filled with the continuous phase, by briefly running the pump at 50 μL/min. For driving the dispersed phase (the Matrigel® suspension), a 1 mL plastic syringe (Terumo) was filled with mineral oil (Sigma, M8410). A 20 GA needle tip (Techcon Systems, TE720050PK) was attached to the syringe, which was installed on a syringe pump (Chemyx, Nexus 3000). The setup was now ready for injection of the Matrigel® suspension.

Right before injection of the suspension, it was homogenized by slowly aspirating and ejecting it using a 100 µL pipette. Using this pipette, 100 µL of the Matrigel® suspension was injected in the inlet of the dispersed phase, and the prepared syringe was inserted in the tube to push the Matrigel® into the cooled tube section. In order to have the complete suspension in the cooled section, the pump was briefly switched on at 20 µL/min.

The chip was first filled with oil: The syringe pump of the continuous phase was turned on at 20 µL/min and left to fill the entire chip with oil and surfactant. After approximately 5 minutes, when oil started to flow from the outlet tube, the flow-rate was reduced to 10 µL/min. The pump for the dispersed phase was set to 5 µL/min, until the Matrigel® suspension had moved to a distance of about 5 mm from the inlet of the chip. The flow-rate of the continuous phase was now set to 2 µL/min, and the flow-rate of the dispersed phase to 1 µL/min. Setting these final flow-rates before the gel entered the chip ensured that the equilibration time of the droplet generating process was minimized.

After the gel had reached the flow-focusing section, the collection of data from the encapsulation process was initiated. Microscopic movies were made with either a regular camera (The Imaging Source, DFK 31AU03), or with a high-speed camera (Vision research, Phantom V9). Regular movies were captured for 30 seconds approximately every 5 minutes, at a frame-rate of 15 Hz. These movies were made of both the flow-focusing section and a section of the meandering channel. High-speed camera movies of the flow-focusing section were captured at a frame-rate of 3000 Hz.

When the last of the Matrigel® had passed the flow-focusing section after approximately 1.5 hours, the pump for the dispersed phase was turned off. The pump for the continuous phase was set to 20 µL/min to remove all remaining beads from the chip.

Figure 13A:
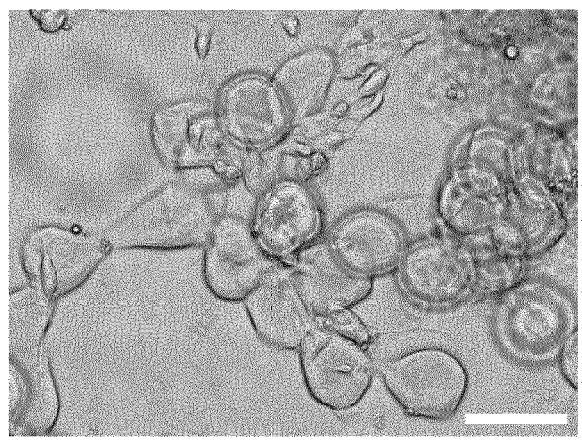
FIGS. 13A-C are images of cell differentiation for cells encapsulated in hydrogel beads.
Figure 13B:
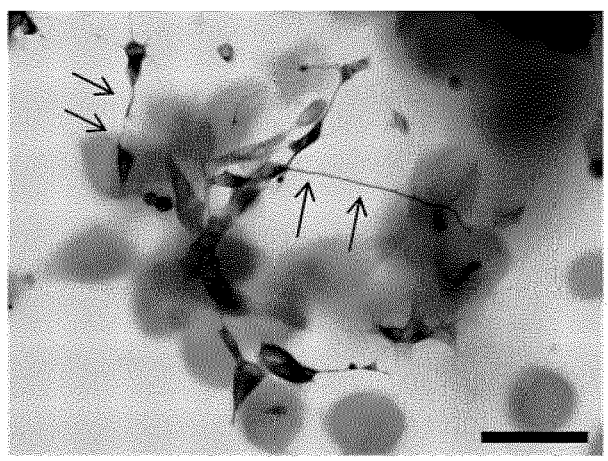
Figure 13C:
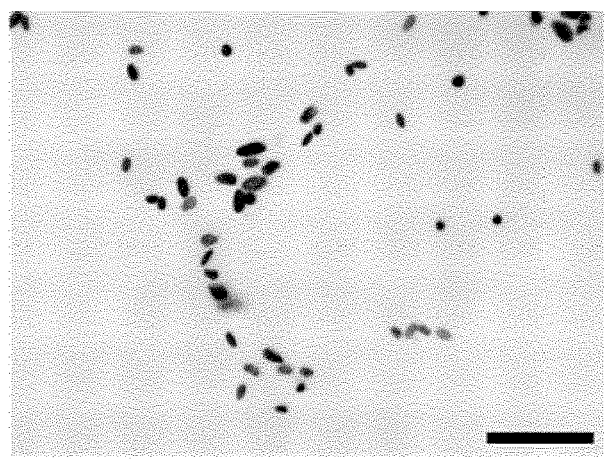
Figure 13D:
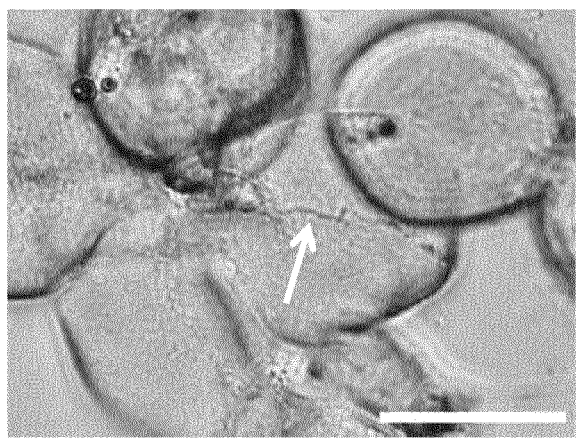
FIGS. 13D-F are further images of cell differentiation for cells encapsulated in hydrogel beads.
Figure 13E:
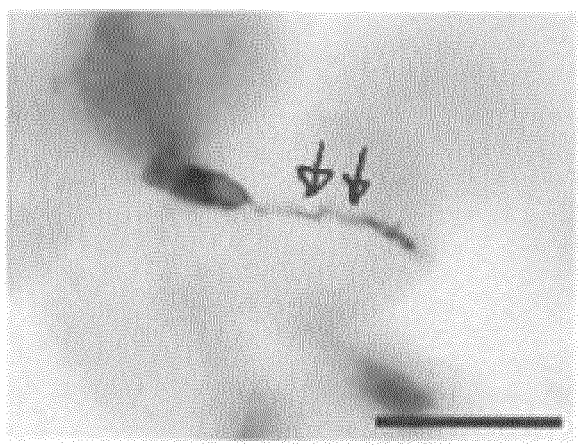
Figure 13F:
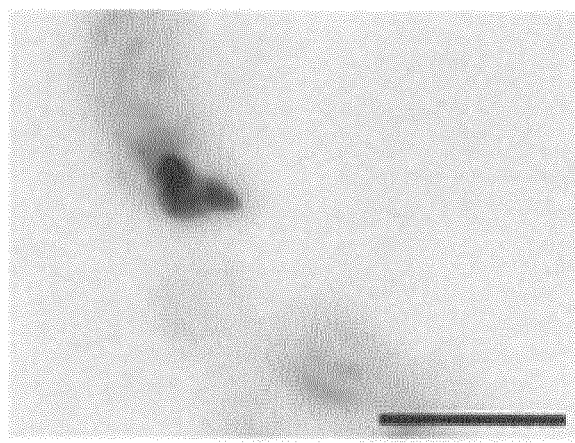

We have seen that cultured cells in hydrogel beads retain differentiation potential. FIGS. 13A-F show this. These are images of differentiated neuronal cell in beads cultured for 10 days before fixing and staining. A phase contrast image (FIG. 13A) shows a group of neuronal cells in gel beads forming a network. An overlay of this image with the neuron-specific staining β-tubulin III (FIG. 13B) confirms that cells indeed differentiated and formed neurites for creating the network. Here the arrows show neuronal processes. Cell nuclei were stained with DAPI (4',6-diamidino-2-phenylindole) (FIG. 13C). Another phase contrast image shows a close-up of differentiated cells with neurites inside beads (FIG. 13D). The overlay with the neuron-specific staining shows the cell body and the formed neuronal process (FIG. 13E) and DAPI was used to stain the nuclei (FIG. 13F). All scale bars indicate 100 µm.

Figure 14A:
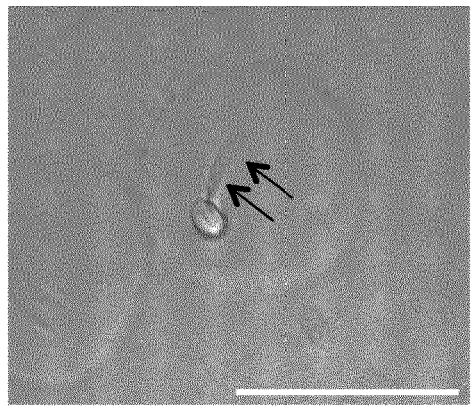
FIGS. 14A-F are further images of cell differentiation for cells encapsulated in hydrogel beads.
Figure 14B:
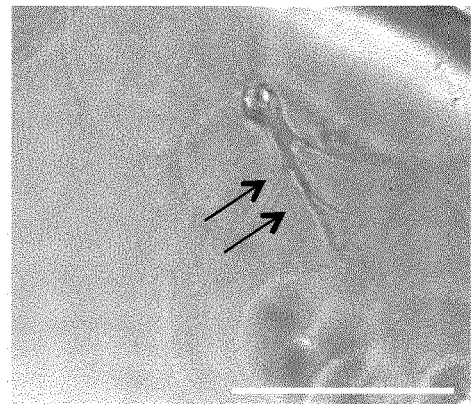
Figure 14C:
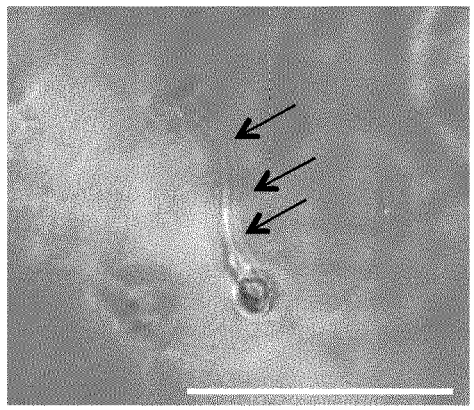
Figure 14D:
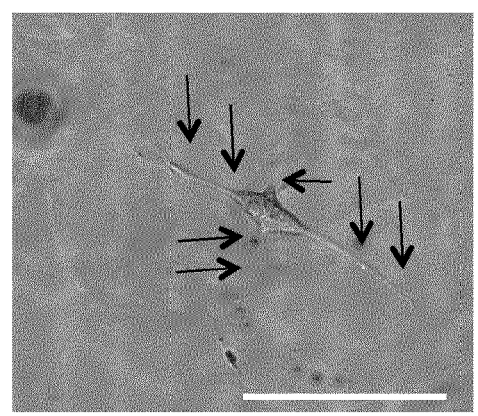
Figure 14E:
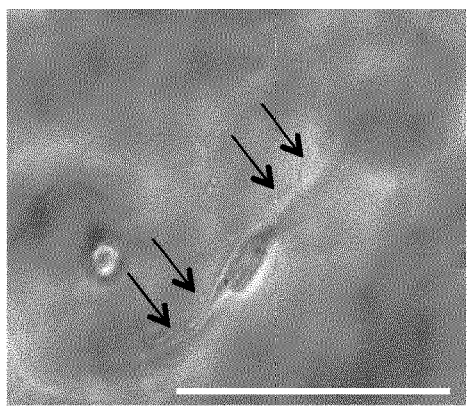
Figure 14F:
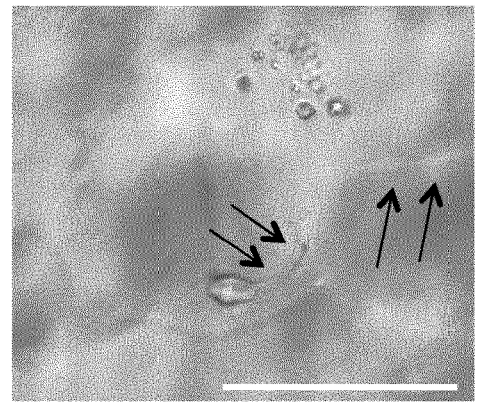

FIGS. 14A-F are further images of cell differentiation for cells encapsulated in hydrogel beads. More specifically, encapsulated SH-SY5Y cells treated with retinoic acid for 72 hours, showing developing neurites, are shown at various days after culturing. FIGS. 14A-C are at day 3, FIG. 14D is at day 4, and FIGS. 14E-F are at day 11. The arrows show neuronal processes. All scale bars indicate 100 µm. SH-SY5Y is a human derived cell line used in scientific research. SH-SY5Y cells are often used as in vitro models of neuronal function and differentiation. They are adrenergic in phenotype but also express dopaminergic markers and, as such, have been used to study Parkinson's Disease.

Further description of these experimental results follows. In order to investigate the ability of Matrigel® beads to self-organize in different environments, several experiments were carried out. The self-assembling properties were investigated in three different environments: mineral oil, cell culture medium, and an evaporative fluorinated oil. Stacking was assessed in mineral oil to test whether beads were monodisperse enough to form a regularly spaced packing. However, for live cell culturing, the encapsulated cells had to be in culture medium, such that nutrient and waste transport was possible. The fluorinated oil was tested based on an approach for evaporative oil removal from the literature, which should enable self-organization in an oil environment, and subsequent transfer to culture medium.

In mineral oil, each bead was surrounded by an oil-water interface, stabilized by a surfactant. As a result, the interaction between particles was repulsive. The driving force for bead sedimentation and packing was provided by gravity, combined with the density difference between the beads (p 1 g/mL) and the surrounding oil (p 0.84 g/mL). Additionally, the beads were deformable, which enabled close packing despite the slight size variation between beads. The combination of this deformity, the driving force, and repulsive interactions resulted in organized stacking of Matrigel® beads with an average diameter of 141 µm and a dispersity of 3.3%.

Both double layers and triple layers of beads were present in the assembly. Locally, the beads had self-organized into a highly ordered hexagonal close packing (HCP) (FIG. 11). A more loose hexagonal double-layered packing was also found. The fact that both loose and tight packing occurred in the same well was likely the result of the oil-air interface, which was curved such that it pushed on the beads in the center of the well.

It is clear that a dispersity of 3.3% or lower is enough to form an organized 3D stacking in mineral oil. However, for cell culturing the beads have to be in medium to facilitate interaction between cells, and nutrient and waste transport. In this situation, the driving force and bead interactions changed, such that the stacking was not as regular (FIG. 12). Only locally and in one layer, some hexagonal ordering was observed.

This can be attributed to several differences between the culture medium and the mineral oil. First, the driving force for sedimentation was a lot less than in mineral oil, due to the smaller density difference between the beads and the surrounding medium: The medium is assumed to have the same density as water ($\rho_w \approx 1$ g/mL), and the Matrigel® density was estimated to be ±1.01 g/mL, based on the average protein concentration of 10 mg/mL.

The driving force can be estimated using Archimedes principle, based on the density of mineral oil, the density of water, and the estimated density of Matrigel®. This results in a driving force of 0.05 nN in medium as opposed to 0.87 nN in mineral oil, indicating a reduction in force of over an order of magnitude.

Second, since the beads are not separated by two oil-water interfaces, matrix proteins in different beads can interact with each other. This makes beads attractive instead of repulsive. Third, the beads do not assume a spherical shape that is as smooth as in mineral oil, which could be the result of plastic deformations during the centrifugation steps, or the lack of an interface that forces the beads in shape by surface tension. Although the deviations seem to be small, it could just be enough to limit the free rotation and movement of the beads. Finally, some of the beads have aggregated into irregular shapes.

For the cell culturing experiments discussed above, it is important to note that not all wells contained an equally high number of beads. Some wells contained only a few beads, which is a result of the manual pipetting steps involved. The samples with high bead density were used for further analysis.

It is clear that the presence of a significant driving force and repulsive bead interactions are important for self-organization. Therefore, a preliminary experiment was carried out to test the assembly in an oil phase, followed by oil removal through evaporation as previously demonstrated in the literature. In order to achieve this, the continuous phase was replaced by perfluoropentane (PFP), which has a boiling point at 29° C., with a PFPE-PEG surfactant to stabilize the beads. Since this oil is much denser than the beads ($\rho_{PFP} \approx 1.63$ g/mL), the beads will rise to the oil-medium interface instead of sinking to the bottom. Unfortunately, some practical difficulties during cell encapsulation in PFP lead to the generation of a very low number of encapsulated cells. Therefore, only a small scale experiment could be carried out. Additionally, the beads were more polydisperse, as a relatively large number of beads was generated in the initial (unstable) phase.

Two different methods of establishing the culture are tested: Pipetting the beads in a µ-plate and then adding medium, or first adding the medium and then the beads. The latter method resulted in the least amount of coalescence, but the reason for this is yet unknown. The beads collected at the oil-water interface, and organized in a similar manner as in mineral oil. The fact that only a single layer of beads is visible can be attributed to the low number of beads in the suspension. The beads seem more deformed than in mineral oil, which could be attributed to three factors. First, the mechanical properties of the beads might have changed, since the encapsulation had to take place at a lower temperature of 20° C. Second, the density difference between the beads and PFP is larger than in mineral oil, which leads to a higher buoyancy force of approximately 3.18 nN as opposed to 0.87 nN in mineral oil. This could have increased the load on the beads, leading to more deformation. Third, the surface tension of PFP is lower than of mineral oil due to the lower surface energy associated with fluorinated materials, which reduces the tension that forces droplets to become spherical.

The beads were left in an incubator at 37° C. and 5% $CO_2$ for 12 hours. Two beads seemed to have moved from the PFP to the culture medium. In one of these beads, a viable cell also seemed to be present. However, lots of beads had coalesced or reduced in size and aggregated. The cells that still remained in these beads were most likely dead, due to nutrient depletion and buildup of toxic metabolites. Apart from this, an oily substance remained in the wells, which was likely the remaining PFPE-PEG surfactant. Clearly, this approach is not yet usable for establishing an organized cell culture in medium. However, the transfer of some beads to medium and the survival of an encapsulated cell seem to indicate that this method could be feasible in the future.

From the performed stacking experiments, we can conclude that full spatial organization of live cells is not yet achievable using one of the tested methods. However, we do show that a culture can be assembled from the encapsulated beads, by transferring them to medium and letting them settle in a µ-slide. Moreover, the stacking experiments in both oils show that high levels of organization can be reached under the right conditions.

The invention claimed is:

1. A method for providing a network of living neuronal cells, the method comprising:
   encapsulating living neuronal cells with a hydrogel to provide hydrogel beads;
   stacking the hydrogel beads in an ordered arrangement within a bioreactor; and
   culturing the ordered arrangement of the hydrogel beads within the bioreactor such that living neuronal cells in different hydrogel beads link with each other to form a network of neuronal cells;
   wherein the encapsulating individual living neuronal cells with a hydrogel to provide hydrogel beads comprises:
   providing a gel precursor + cells first mixture to a microfluidic apparatus;
   providing an oil + surfactant second mixture to the microfluidic apparatus;
   wherein the second mixture separates zones of the first mixture;
   wherein the microfluidic apparatus includes a cold zone where the first and second mixtures are input and a warm zone where the gel precursor changes from a liquid to a gel.

2. The method of claim 1, wherein the cold zone has a temperature in a range from 1-4° C. and wherein the warm zone has a temperature in a range from 10-38° C.

3. The method of claim 1, wherein the microfluidic apparatus is integrated with the bioreactor.

4. The method of claim 1, wherein the encapsulated living neuronal cells differentiate during the culturing the ordered arrangement of the hydrogel beads within the bioreactor.

5. The method of claim 1, wherein the bioreactor further comprises one or more electrodes configured to make electrical contact with the network of neuronal cells.

6. The method of claim 5, wherein the bioreactor further comprises one or more living cells disposed on at least one of the electrodes and configured to act as transducer cells for the network of neuronal cells.

7. The method of claim 5, further comprising performing an electrophysiological assay of the network of neuronal cells vs. a target analyte.

8. The method of claim 1, further comprising performing an assay of the network of neuronal cells vs. a target analyte.

9. The method of claim 8 wherein the assay is a biological assay and wherein the target analyte is a biological species.

10. The method of claim 8, wherein the assay is a chemical assay and wherein the target analyte is a chemical species.

11. The method of claim 8, wherein the assay is a physical assay and wherein the target analyte is a physical stimulus.

12. The method of claim 8, wherein the assay of the network of neuronal cells includes an evaluation of a number of neuronal connections formed in the presence of the target analyte.

13. The method of claim 8, wherein the assay of the network of neuronal cells includes an evaluation of disorder of the network of neuronal cells in the presence of the target analyte.

* * * * *